United States Patent [19]
Aeschlimann

[11] Patent Number: 6,033,443
[45] Date of Patent: *Mar. 7, 2000

[54] PROCESS FOR TREATING CELLULOSE FIBRES

[75] Inventor: Peter Aeschlimann, Allschwil, Switzerland

[73] Assignee: Ciba Specialty Chemicals Corporation, Tarrytown, N.Y.

[ * ] Notice: This patent is subject to a terminal disclaimer.

[21] Appl. No.: 09/153,736

[22] Filed: Sep. 15, 1998

[30] Foreign Application Priority Data

Sep. 17, 1997 [EP] European Pat. Off. .............. 97810671
Mar. 25, 1998 [CH] Switzerland .............. 705/98

[51] Int. Cl.$^7$ ................. D06M 13/358; C07D 251/28; C07D 251/44; D06P 1/642
[52] U.S. Cl. ................ 8/190; 8/120; 8/196; 8/116.1; 8/495; 8/566; 8/688; 8/494; 427/388.2; 427/388.4; 427/389.9; 427/393.2; 427/394
[58] Field of Search ................ 8/190, 120, 196, 8/116.1, 495, 566, 688, 494; 427/388.2, 388.4, 389.9, 393.2, 394

[56] References Cited

U.S. PATENT DOCUMENTS

| 3,074,814 | 1/1963 | Sause et al. . |
| 3,124,414 | 3/1964 | Dolmetsch . |

FOREIGN PATENT DOCUMENTS

| 0538977 | 4/1993 | European Pat. Off. . |
| 538977 | 4/1993 | European Pat. Off. . |
| 0616071 | 9/1994 | European Pat. Off. . |
| 1243816 | 1/1961 | France . |
| 1085492 | 7/1960 | Germany . |
| 4308075 | 9/1994 | Germany . |
| 39-14644 | 7/1964 | Japan . |
| 869660 | 6/1961 | United Kingdom . |
| 880624 | 10/1961 | United Kingdom . |
| 896814 | 5/1962 | United Kingdom . |
| 1285450 | 8/1972 | United Kingdom . |
| 92/07124 | 4/1992 | WIPO . |
| 94/09191 | 4/1994 | WIPO . |
| 97/49856 | 12/1997 | WIPO . |

OTHER PUBLICATIONS

Derwent Abstr. 81–18088D.

*Primary Examiner*—Alan Diamond
*Attorney, Agent, or Firm*—Kevin T. Mansfield

[57] ABSTRACT

This invention relates to a process for treating Lyocell cellulose fibers, which comprises treating the Lyocell cellulose fiber with at least one compound of formula

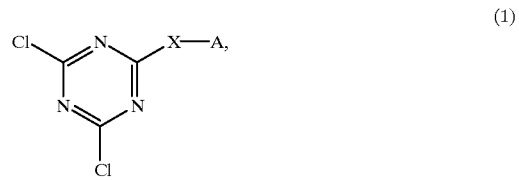

(1)

wherein
X is —NR— or —S—, A is an aliphatic radical containing 1 to 18 carbon atoms which is free of sulfo groups, or —X—A is hydroxy, and R is hydrogen or, independently of A, has the meaning of A.

15 Claims, No Drawings

PROCESS FOR TREATING CELLULOSE FIBRES

The present invention relates to a process for reducing the fibrillation tendency in Lyocell cellulose fibres.

Lyocell fibres are fibres which are obtained by a process in which the cellulose is dissolved in an organic solvent, in a combination of an organic solvent with an inorganic salt or in aqueous salt solutions, and is then spun from this solution.

However, the usefulness of the fabrics, e.g. textile materials, prepared from said fibres is severely limited by the strong tendency of these fibres to fibrillate in the wet state. Fibrillation is understood as meaning the breaking up of the wet fibre in the longitudinal direction under mechanical stress up to the point of fibrils detaching along the fibre surface, giving the fibre a hairy or furry look. Furthermore, a fabric produced from such fibres loses much of its colour intensity after being washed several times.

There is therefore a need for a process which reduces the fibrillation in Lyocell fibres or suppresses it completely.

Surprisingly, it has been found that the process of this invention strongly reduces the fibrillation tendency of the treated Lyocell fibres.

Accordingly, this invention relates to a process for treating Lyocell cellulose fibres, which comprises treating the Lyocell cellulose fibre with at least one compound of formula

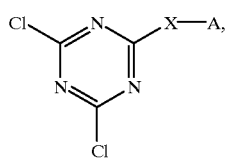

(1)

wherein

X is —NR— or —S—,

A is an aliphatic radical containing 1 to 18 carbon atoms which is free of sulfo groups, or —X—A is hydroxy, and R is hydrogen or, independently of A, has the meaning of A.

The Lyocell cellulose fibre is usually treated with at least one compound of formula (1), wherein X is —NR— or —S—, A is an aliphatic radical containing 1 to 18 carbon atoms which is free of sulfo groups, and R is hydrogen or, independently of A, has the meaning of A.

A defined as aliphatic radical containing 1 to 18 carbon atoms is, for example, a $C_1$–$C_{18}$alkyl radical, typically methyl, ethyl, n-propyl, isopropyl, n-butyl, sec-butyl, tert-butyl, isobutyl, pentyl, hexyl, heptyl, octyl, nonyl, decyl, dodecyl, tetradecyl, hexadecyl, heptadecyl or octadecyl, wherein the alkyl radical may be substituted, e.g. by hydroxy or alkoxy, and wherein the alkyl chain may be interrupted once of several times, for example by oxygen, sulfur, amino, carbonamido, aminocarbonyl, ureido, sulfonamido, aminosulfonyl, carboxy and carbonyloxy.

A is preferably linear or branched $C_1$–$C_{18}$alkyl, more preferably $OR_1$-substituted $C_1$–$C_8$alkyl, wherein the alkyl chain may be interrupted by one or several radicals —Q—, or linear or branched $C_1$–$C_{18}$alkyl, more preferably $C_1$–$C_8$alkyl, wherein the alkyl chain is interrupted by one or several radicals —Q—, where —Q— is —O—, —S—, —$NR_2$—, —$CONR_2$—, —$NR_2CO$—, —$NR_2$—CO—$NR_3$—, —$SO_2NR_2$—, —$NR_2SO_2$—, —COO—, —OCO—, —$NR_2COO$— or —OCOO—, $R_1$ is hydrogen or $C_1$–$C_4$alkyl, $R_2$ is hydrogen or $C_1$–$C_4$alkyl, and $R_3$ is hydrogen or $C_1$–$C_4$alkyl.

A defined as $C_1$–$C_{18}$alkyl or $C_1$–$C_8$alkyl may additionally be mono- or polysubstituted by e.g. carboxy, carbonamido or sulfonamido.

X is preferably —NR—.

R having the meaning of A is preferably $C_1$–$C_4$alkyl, such as methyl, ethyl, n-propyl, isopropyl, n-butyl, sec-butyl, tert-butyl or isobutyl.

R is particularly preferably methyl and, most preferably, hydrogen.

$R_1$ defined as $C_1$–$C_4$alkyl is methyl, ethyl, n-propyl, isopropyl, n-butyl, sec-butyl, tert-butyl or isobutyl.

$R_2$ and $R_3$ defined as $C_1$–$C_4$alkyl are methyl, ethyl, n-propyl, isopropyl, n-butyl, sec-butyl, tert-butyl, or isobutyl.

$R_1$ is preferably methyl and, most preferably, hydrogen. $R_2$ is preferably hydrogen. $R_3$ is preferably hydrogen. —Q— is preferably —O—, —S— and —NH—.

Compounds which are particularly interesting for the novel process are those of formula (1), wherein —X—A is the following radicals: —$NHCH_2CH_2SCH_2CH_2OH$, —$NHCH_2CH_2CONHCH_2CH_2OH$, —$NHCH_2CH_2CH_2CONHCH_2CH_2OH$, —$NHCH_2CONHCH_2CH_2CH_2OH$, —$NHCH_2CONHCH_2CH_2CH_2OH$, —$NHCH_2CON(CH_2CH_2OH)_2$, —$NHCH_2CH_2NHCOCH_2CH_2CH_2OH$, —$NHCH_2CH_2CH_2NHCOCH_2CH_2CH_2OH$, and —$NHCH_2CH_2CH_2CONHCH_2CH_2CH_2OH$.

Compounds which are particularly important for the novel process are those of formula (1), wherein —X—A is the following radicals:

—$NHCH_2CH_2SCH_2CH_2OH$,
—$NHCH_2CH_2CONHCH_2CH_2OH$,
—$NHCH_2CH_2CH_2CONHCH_2CH_2OH$,
—$NHCH_2CONHCH_2CH_2CH_2OH$,
—$NHCH_2CONHCH_2CH_2CH_2OH$, —$NHCH_2CON(CH_2CH_2OH)_2$,
—$NHCH_2CH_2NHCOCH_2CH_2CH_2OH$,
—$NHCH_2CH_2CH_2NHCOCH_2CH_2CH_2OH$, and
—$NHCH_2CH_2CH_2CONHCH_2CH_2CH_2OH$.

Compounds which are particularly important for the novel process are those of formulae

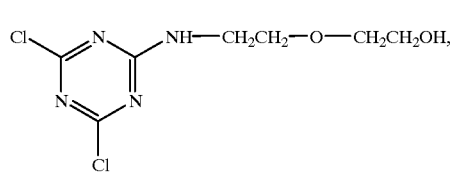

(2)

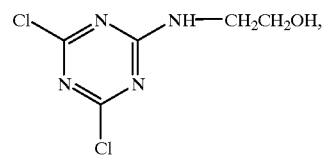

(3)

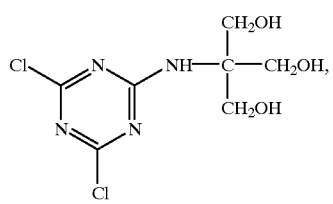 (4)
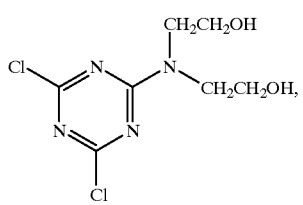 (5)
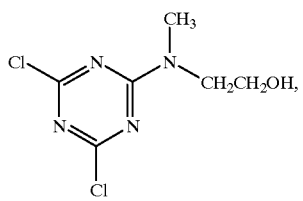 (6)
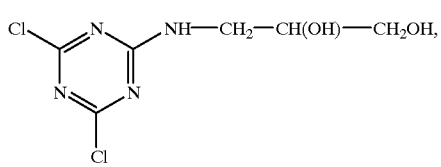 (7)
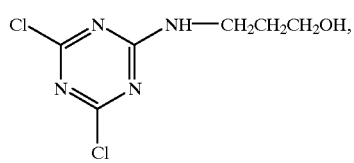 (8)
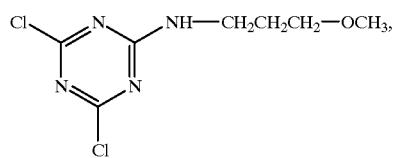 (9)
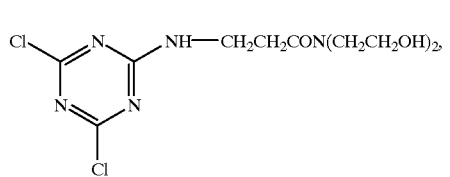 (10)
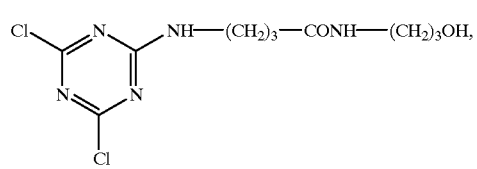 (11)
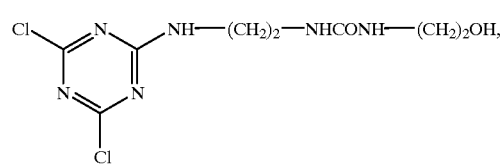 (12)
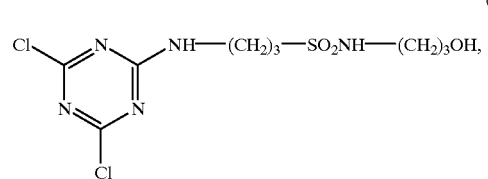 (13)
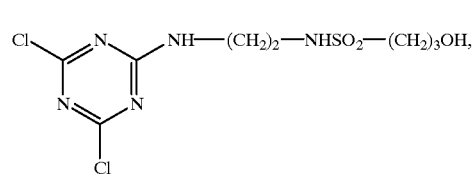 (14)
and
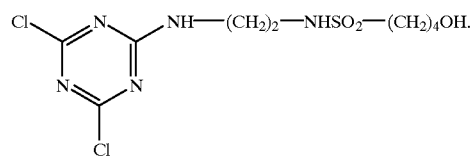 (15)
Another particularly important compound for the novel process is that of formula
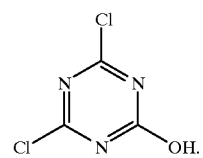 (16)
The compounds of formulae (2) and (3) are very particularly important for the novel process.
The compounds of formulae (2), (7) and (10) to (15) are novel and are another subject matter of this invention.

The compounds of formula (1) used in the process of this invention are prepared by methods known per se, for example by reacting a trichlorotriazine of formula

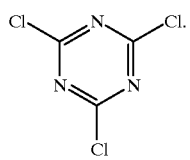
(20)

with an equimolar amount of a compound of formula

HX—A    (21), wherein X and A have the meaning given for formula (1), and then isolating the resulting final product of formula (1).

The preparation of the novel compounds of formulae (2), (7) and (10) to (15) is carried out in analogous manner by reacting a trichlorotriazine of formula (20) with an amine of formula

NH$_2$—CH$_2$CH$_2$OCH$_2$CH$_2$OH,    (22)

NH$_2$—CH$_2$CH(OH)CH$_2$OH,    (23)

NH$_2$—CH$_2$CH$_2$CON(CH$_2$CH$_2$OH)$_2$,    (24)

NH$_2$—CH$_2$CH$_2$CH$_2$CONHCH$_2$CH$_2$CH$_2$OH,    (25)

NH$_2$—CH$_2$CH$_2$NHCONHCH$_2$CH$_2$OH,    (26)

NH$_2$—CH$_2$CH$_2$CH$_2$SO$_2$NHCH$_2$CH$_2$CH$_2$OH,    (27)

NH$_2$—CH$_2$CH$_2$NHSO$_2$CH$_2$CH$_2$CH$_2$OH or    (28)

NH$_2$—CH$_2$CH$_2$NHSO$_2$CH$_2$CH$_2$CH$_2$CH$_2$OH.    (29)

Some of the amines of formulae (22) to (29) are known or they can be prepared by methods known per se.

A useful embodiment of the novel process comprises treating the Lyocell cellulose fibres in alkaline milieu with the compounds of this invention. The alkaline milieu is preferably formed by an alkali carbonate and/or an alkali hydroxide. The treatment can be carried out on undyed fibres as well as on fibres which are to be dyed, before, during or immediately after a dyeing process.

If the inventive compounds are applied to undyed fibres, then they are applied either by a treatment bath or directly after the spinning process to the freshly spun and not yet dried fibres (so-called never-dried fibres as described, inter alia, in EP-A-0 538 977, page 4, or in U.S. Pat. No. 5,580,354, column 4).

If the inventive compounds are used in the course of a dyeing process, then they are expediently used before or during the actual dyeing process.

The compounds used according to this invention can be applied to the fibre in a separate treatment bath or, preferably, together with the dyes used in a dye bath under the respective dyeing conditions.

If the compounds used according to this invention are applied to the fibre from a separate treatment bath, then this may be done at a temperature in the range from 15 to 140° C., preferably from 40 to 100° C. over 10 to 120 minutes, preferably over 30 to 90 minutes. Another advantageous embodiment of the novel process consists in wetting the fibres to be treated with an aqueous solution of the compounds of this invention and then subjecting them to a steam treatment for 5 to 60 seconds, preferably for 10 to 30 seconds, at 90 to 130° C. The fibre can be wetted by immersion in a bath as well as by being sprayed.

The Lyocell cellulose fibres can be obtained and treated as such, as yarn or in the form of fabrics, such as wovens or knit fabrics.

The compounds of this invention are normally used in the treatment liquors or dyeing liquors in amounts from 0.1 to 15% by weight, preferably from 1 to 10% by weight, particularly preferably from 2 and 6% by weight, based on the weight of the fibre.

In another of its aspects, this invention relates to the use of the compounds of formula (1) for reducing the fibrillation in Lyocell cellulose.

The fibrillation tendency of the untreated and treated fibres is assessed by a modified Martindale wet abrasion test in which the wetted fabric sample is abraded under defined stress until first formation of holes. The number of the abrasion runs until holes form gives the wet abrasion resistance which serves as a measure of the fibrillation.

The invention is illustrated by the following Examples. Temperatures are given in degrees Celsius and parts and percentages are by weight, unless otherwise stated. The ratio of parts by weight to parts by volume is that of the kilogramme to the liter.

EXAMPLE 1

18.5 g of cyanuric chloride are added to a mixture consisting of 100 g of finely ground ice and 50 ml of water containing 0.6 g of a commercially available surfactant and are wetted for 15 minutes. With vigorous stirring, 6.1 g of ethanolamine are then added dropwise such that the pH of the mixture is kept at about 8. After the addition of ethanolamine is complete, about 8 g of a 50% aqueous solution of NaOH are added dropwise such that the pH can be kept at 8. The resulting fine suspension is filtered and dried, giving 15.5 g of a white powdered compound of formula

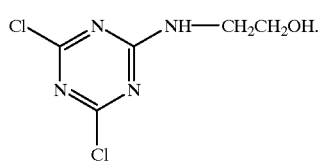
(3)

EXAMPLES 2 to 9

The procedure of Example 1 is repeated, but replacing 6.1 g of ethanolamine with the equivalent amount of one of the amines of formulae (22) to (29), giving the compounds of formulae (2), (7) and (10) to (15) which are compiled in Table 1.

TABLE 1

| Amine of formula | No. | Compound of formula | No. |
|---|---|---|---|
| $NH_2-CH_2CH_2OCH_2CH_2OH$ | (22) | 4,6-dichloro-1,3,5-triazin-2-yl−NH−$CH_2CH_2$−O−$CH_2CH_2OH$ | (2) |
| $NH_2-CH_2CH(OH)CH_2OH$ | (23) | 4,6-dichloro-1,3,5-triazin-2-yl−NH−$CH_2$−CH(OH)−$CH_2OH$ | (7) |
| $NH_2-CH_2CH_2CON(CH_2CH_2OH)_2$ | (24) | 4,6-dichloro-1,3,5-triazin-2-yl−NH−$CH_2CH_2CON(CH_2CH_2OH)_2$ | (10) |
| $NH_2-CH_2CH_2CH_2CONHCH_2CH_2CH_2OH$ | (25) | 4,6-dichloro-1,3,5-triazin-2-yl−NH−$(CH_2)_3$−CONH−$(CH_2)_3OH$ | (11) |
| $NH_2-CH_2CH_2NHCONHCH_2CH_2OH$ | (26) | 4,6-dichloro-1,3,5-triazin-2-yl−NH−$(CH_2)_2$−NHCONH−$(CH_2)_2OH$ | (12) |
| $NH_2-CH_2CH_2CH_2SO_2NHCH_2CH_2CH_2OH$ | (27) | 4,6-dichloro-1,3,5-triazin-2-yl−NH−$(CH_2)_3$−$SO_2NH$−$(CH_2)_3OH$ | (13) |
| $NH_2-CH_2CH_2NHSO_2CH_2CH_2CH_2OH$ | (28) | 4,6-dichloro-1,3,5-triazin-2-yl−NH−$(CH_2)_2$−$NHSO_2$−$(CH_2)_3OH$ | (14) |
| $NH_2-CH_2CH_2NHSO_2CH_2CH_2CH_2CH_2OH$ | (29) | 4,6-dichloro-1,3,5-triazin-2-yl−NH−$(CH_2)_2$−$NHSO_2$−$(CH_2)_4OH$ | (15) |

Note: the "Compound of formula" entries are each a 2,4-dichloro-1,3,5-triazine substituted at the 6-position with the indicated −NH−R group (shown as a triazine ring with two Cl substituents in the original).

EXAMPLE 10

A laboratory dyeing apparatus is charged with a liquor consisting of 50 ml of water and 15 ml of a 20% aqueous solution of sodium sulfate and this mixture is heated to 50° C. A 10 g piece of Lyocell fabric is then immersed in the liquor and the temperature is raised to 90° C. at a gradient of 2° C./min. During the heating-up stage, 0.6 g of the compound of formula (3), dissolved in 27.5 ml of water, are added at 70° C. The Lyocell fabric is treated for 60 minutes at 90° C. The treatment liquor is cooled to 70° C. and charged with 7.5 ml of a 20% aqueous soda solution and is then kept for another 45 minutes at 70° C.

The bath is drained off and the treated Lyocell fabric is rinsed with water and then boiled for 5 minutes in a fresh, purely aqueous bath, rinsed again cold and dried.

In a Martindale wet abrasion test, the dried Lyocell fabric shows about double the number of abrasion runs as compared to untreated Lyocell fabric.

In this application the Lyocell fabric can also be simultaneously dyed by adding one or several reactive dyes immediately after the addition of the compound of formula (3).

The procedure of Example 10 is repeated, but replacing 0.6 g of the compound of formula (3) with the same amount of one of the compounds of formula (2) or (4) to (15), which also gives a Lyocell fabric having high Martindale wet abrasion values.

EXAMPLE 11

A laboratory dyeing apparatus is charged with a liquor consisting of 50 ml of water and 15 ml of a 20% aqueous solution of sodium sulfate and this mixture is heated to 60° C. A 10 g piece of Lyocell fabric is then immersed in the liquor, adding 3 minutes later 0.6 g of the compound of formula (3), dissolved in 25.5 ml of water. After another 15 minutes, 7.5 ml of a 20% aqueous soda solution are added to the liquor which is then kept at 60° C. for 30 minutes.

The liquor is then charged with 2 ml of a 3% aqueous NaOH solution and is kept for another 10 minutes at 60° C. The Lyocell fabric is then finished as described in Example 2. The finished Lyocell fabric may then be dyed by a customary process, for example with reactive dyes.

In a Martindale wet abrasion test, the dried Lyocell fabric shows about double the number of abrasion runs as compared to untreated Lyocell fabric.

The procedure of Example 11 is repeated, but replacing 0.6 g of the compound of formula (3) with the same amount of one of the compounds of formula (2) or (4) to (15), which also gives a Lyocell fabric having high Martindale wet abrasion values.

EXAMPLE 12

A liquor comprising 42 g/l of a compound of formula

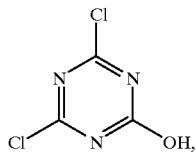

(16)

70 ml/l of sodium silicate (38° Bé), 33 ml/l of an aqueous sodium hydroxide solution (36° Bé), and 1 g/l of a commercially available wetting agent, is padded to a Lyocell fabric (liquor pick-up 70%). Without drying, the Lyocell fabric thus treated is further treated directly for 8 minutes in saturated steam of 102° C. The Lyocell fabric is then rinsed with water, boiled in a fresh, purely aqueous bath for 5 minutes, rinsed cold and dried.

In a Martindale wet abrasion test, the treated Lyocell fabric shows an about 2.5-fold number of abrasion runs as compared to untreated Lyocell fabric.

EXAMPLE 13

A laboratory dyeing apparatus is charged with a liquor consisting of 35 ml of water and 30 ml of a 20% aqueous solution of sodium sulfate and this mixture is heated to 80° C. A 10 g piece of Lyocell fabric is then immersed in this liquor, adding after 5 minutes 0.5 g of the compound of formula (16), dissolved in 20 ml of water. After another 15 minutes, the liquor is charged with 5 ml of a 20% aqueous soda solution. After another 5 minutes, 5 ml of a 3% aqueous NaOH solution are added, and after another 5 minutes another 5 ml of a 3% aqueous NaOH solution are added. The liquor is then kept at 80° C. for 30 minutes.

The bath is then drained off and the treated Lyocell fabric is rinsed with water and then boiled for 5 minutes in a fresh, purely aqueous bath, rinsed again cold and dried. In a Martindale wet abrasion test, the dried Lyocell fabric shows more than double the number of abrasion runs as compared to untreated Lyocell fabric.

What is claimed is:

1. A process for reducing the fibrillation of Lyocell cellulose fibres, which comprises contacting the Lyocell cellulose fibres with at least one compound of formula

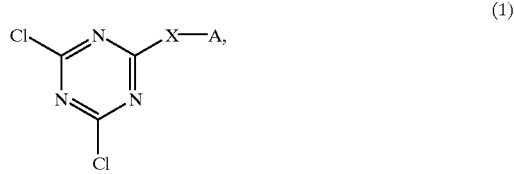

(1)

wherein

X is —NR— or —S—, A is an aliphatic radical containing 1 to 18 carbon atoms which is free of sulfo— groups, or —X—A is hydroxy, and R is hydrogen or, independently of A, has the meaning of A, whereby fibrillation in the Lyocell cellulose fibres is reduced.

2. A process according to claim 1, which comprises contacting the Lyocell cellulose fibre with at least one compound of formula (1), wherein X is —NR— or —S—, A is an aliphatic radical containing 1 to 18 carbon atoms which is free of sulfo groups, and R is hydrogen or, independently of A, has the meaning of A.

3. A process according to claim 1, which comprises contacting the Lyocell cellulose fibre with a compound of formula

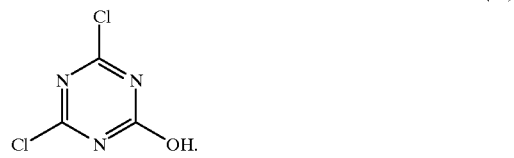

(16)

4. A process according to claim 1, wherein A is $OR_1$-substituted $C_1$–$C_{18}$-alkyl, wherein the alkyl chain is optionally interrupted by one or more radicals —Q—, or $C_1$–$C_{18}$-alkyl, wherein the alkyl chain is interrupted by one or more radicals —Q—, where —Q— is —O—, —S—, —$NR_2$—, —$CONR_2$—, —$NR_2CO$—, —$NR_2$—CO—$NR_3$—, —$SO_2NR_2$—, —$NR_2SO_2$—, —COO—, —OCO—, —$NR_2COO$— or —OCOO—, and $R_1$ is hydrogen or $C_1$–$C_4$alkyl, $R_2$ is hydrogen or $C_1$–$C_4$alkyl, and $R_3$ is hydrogen or $C_1$–$C_4$alkyl.

5. A process according to claim 4, wherein A is $OR_1$-substituted $C_1$–$C_8$alkyl, wherein the alkyl chain is optionally interrupted by one or more radicals —Q—, or $C_1$–$C_8$alkyl, wherein the alkyl chain is interrupted by one or more radicals —Q—, where —Q— is —O—, —S—, —$NR_2$—, —$CONR_2$—, —$NR_2CO$—, —$NR_2$—CO—$NR_3$—, —SO$_2$NR$_2$—, —NR$_2$SO$_2$—, —COO—, —OCO—, —NR$_2$COO— or —OCOO—, and R$_1$ is hydrogen or C$_1$–C$_4$-alkyl, R$_2$ is hydrogen or C$_1$–C$_4$alkyl, and R$_3$ is hydrogen or C$_1$–C$_4$alkyl.

6. A process according to claim 1, wherein X is —NR—.

7. A process according to claim 4, wherein —Q— is —O—, —S— or —NR$_2$—.

8. A process according to claim 1, which comprises using the compound of formula

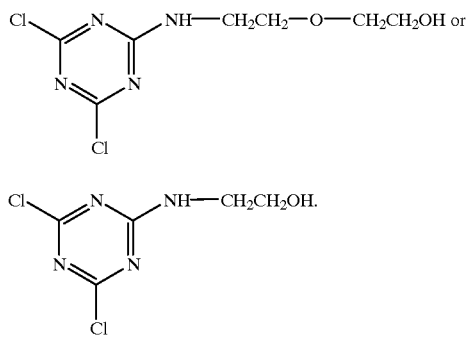

9. A process according to claim 1, which comprises using from 0.1 to 15% by weight of the compound of formula (1), based on the weight of the fibre.

10. A process according to claim 3, which comprises using from 0.1 to 15% by weight of the compound of formula (16), based on the weight of the fibre.

11. A process according to claim 8, which comprises using from 0.1 to 15% by weight of one of the compounds of formula (2) or (3), based on the weight of the fibre.

12. A process according to claim 1, which comprises applying the compound of formula (1) to freshly spun never-dried fibre.

13. A process according to claim 3, which comprises applying the compound of formula (16) to freshly spun never-dried fibre.

14. A process according to claim 8, which comprises applying one of the compounds of formula (2) or (3) to freshly spun never-dried fibre.

15. A process according to claim 1, which comprises applying the compound of formula (1) to the fibre before or during a dyeing process.

* * * * *